「United States Patent [19]
McCrea et al.

[11] Patent Number: 5,292,530
[45] Date of Patent: Mar. 8, 1994

[54] STABLE ANHYDROUS TOPICALLY-ACTIVE COMPOSITION AND SUSPENDING AGENT THEREFOR

[75] Inventors: Andrew D. McCrea, Chicago; Michael P. Diulus, Oak Park, both of Ill.

[73] Assignee: Helene Curtis, Inc., Chicago, Ill.

[21] Appl. No.: 770,888

[22] Filed: Oct. 4, 1991

Related U.S. Application Data

[63] Continuation-in-part of Ser. No. 360,418, Jun. 2, 1991.

[51] Int. Cl.$^5$ .......................... A61K 7/34; A61K 7/38; A61K 7/42; A61K 7/48
[52] U.S. Cl. ................... 424/066; 252/363.5; 424/47; 424/59; 424/68; 514/817; 514/844; 514/852; 514/859; 514/861; 514/863; 514/864; 514/880; 514/887
[58] Field of Search .................................... 424/59, 66

[56] References Cited
FOREIGN PATENT DOCUMENTS
0028853 5/1981 European Pat. Off. .............. 424/68

Primary Examiner—Dale R. Ore
Attorney, Agent, or Firm—Marshall, O'Toole, Gerstein, Murray & Borun

[57] ABSTRACT

An anhydrous, topically-effective composition that resists phase separation and exhibits improved properties comprising a topically-active compound, such as an astringent salt; an improved suspending agent comprising a finely-divided silica and a suspending wax composition; and a suitable volatile liquid carrier, such as a volatile silicone or a volatile hydrocarbon. The suspending wax composition comprises a wax, an ester including at least 10 to about 32 carbon atoms and a volatile liquid carrier. The anhydrous, topically-effective composition is useful in topical cosmetic and medicinal preparations, such as antiperspirants, sunscreens and topical drug products, and is especially useful in cosmetic and medicinal preparations wherein an insoluble topically-active compound is dispersed throughout a liquid phase.

46 Claims, No Drawings

STABLE ANHYDROUS TOPICALLY-ACTIVE COMPOSITION AND SUSPENDING AGENT THEREFOR

CROSS-REFERENCE TO A RELATED APPLICATION

This application is a continuation-in-part of copending application Ser. No. 360,418, filed on Jun. 2, 1991.

FIELD OF THE INVENTION

The present invention is directed to an anhydrous composition including a new and improved suspending agent, wherein the anhydrous composition effectively resists phase separation and is useful for the topical delivery of a topically-active component. More particularly, the anhydrous composition of the present invention is an unexpectedly stable suspension useful for the improved topical delivery of a topically-active compound, either cosmetic or medicinal, to the skin. Therefore, in general, the present invention is directed to an anhydrous, topically-effective composition comprising a topically-active compound, such as an antiperspirant compound, like a powdered astringent salt; a suspending agent including a finely-divided silica and a suspending wax composition; and a suitable volatile liquid carrier. The topically-effective composition effectively resists phase separation; reduces whitening and staining to skin and clothing after topical application; effectively delivers the topically-active compound; and exhibits superior sensory properties.

BACKGROUND OF THE INVENTION

As set forth in the Deckner U.S. Pat. No. 4,563,346, an ideal composition for delivery a topically-active compound to skin or hair should be stable and should deliver the topically-active compound such that it adheres to the skin or hair while topically-inactive ingredients evaporate or are otherwise removed from the area of application. Topically-delivered active compounds, such as cosmetics, like an antiperspirant compound, and topical medications, like an antibacterial or an anti-inflammatory, traditionally have been prepared as either oil-in-water emulsions or water-in-oil emulsions. However, topically-effective compositions prepared as emulsions feel wet or oily when applied to the skin, and often remain sticky after the composition carrier vehicle evaporates. Furthermore, emulsion-type compositions require a relatively long time to dry after topically application. In addition, many emulsion-type compositions leave a white residue on contacted skin or clothing, and actually stain clothing.

Nonemulsified anhydrous compositions, like antiperspirants, are known in the art. For example, non-emulsified, oil-based topically-effective compositions are available, however these products often require shaking prior to each use in order to redisperse the insoluble topically-active compound that has separated from the composition. For example, U.S. Pat. No. 3,873,686 discloses an anhydrous, liquid or cream antiperspirant composition comprising an alcohol-soluble aluminum chlorohydroxide-polyol complex in an anhydrous ethanol vehicle. Similarly, U.S. Pat. No. 4,137,306 discloses the above-described anhydrous antiperspirant composition in solid stick form. U.S. Pat. Nos. 4,053,581; 4,065,564; and 4,073,880 disclose liquid anhydrous antiperspirant compositions useful as pump-spray and roll-on products, wherein the antiperspirant compounds are solubilized in a vehicle including ethanol and a sufficient amount of a volatile or a non-volatile silicone liquid to reduce tackiness of the antiperspirant. U.K. Patent Application No. 2018590A describes an anhydrous antiperspirant spray composition including from 60% to 90% of a volatile cyclic silicone in order to improve composition efficacy by increasing adherence of the antiperspirant composition to the skin and hair. Nevertheless, although suspending agents are included in each of the above-cited references, the antiperspirant compositions require shaking before use in order to redisperse the separated antiperspirant compound.

Stable, nonseparating antiperspirant compositions also are known in the art. U.S. Pat. No. 4,749,569 discloses an extrudable antiperspirant paste, or cream, composition stabilized against phase separation by thickening the antiperspirant composition with from 4.6% to 9.5% of a finely-divided silica and from 2% to 25% of a quaternized three-layer clay exfoliated with a polar solvent. If a finely-divided silica is used as the sole thickening, or suspending, agent, then an unstable product results. Therefore, an additional suspending agent, like an organoclay, is included in the composition. However, the presence of an organoclay in an antiperspirant composition is a principal source of the whitening and staining of the skin and clothing.

Nabial, in U.S. Pat. No. 4,425,328, discloses a stick antiperspirant composition including a volatile silicone; a relatively high amount of a waxy matrix, i.e. from about 17 to 30 percent by weight; and a suspending agent to suspend the antiperspirant compound. Nabial specifically discloses using a clay as a suspending agent for the disclosed solid compositions. In contrast, the present compositions are stable liquid or flowable semisolid products that effectively resist phase separation by including a relatively low amount of a wax, i.e. up to about 4.5% by weight of the composition. Furthermore, an important feature of the present invention is to provide a composition absent a clay suspending agent that stains the skin and clothing.

Davy et al. U.S. Pat. No. 4,126,679 discloses a cosmetic stick composition. The Davy et al. composition includes from about 15% to about 70% of a long chain alcohol having 16 to 22 carbon atoms. The long chain alcohol is a wax, and the relatively high amount of the long chain alcohol suspends the other ingredients in the stick composition. In contrast, the present liquid or flowable semisolid composition includes no more than about 4.5% by weight of a wax, and, surprisingly, exhibits essentially no phase separation after long storage periods.

Bissett et al., in European Patent Application No. 88309740.4, disclose pharmaceutical and cosmetic compositions including tocopherol sorbate for topical application to the skin. The Bissett et al. application is directed to compositions that protect the skin from the harmful effects of sunbathing. Bissett et al. do not teach a stable liquid or cream composition comprising a topically-active compound and a suspending agent including a finely-divided silica and a suspending wax composition, wherein the composition resists phase separation and is nonwhitening and nonstaining to skin and clothing.

Palinczar, in U.S. Pat. No. 4,724,139, discloses an antiperspirant composition including a volatile isoparaffin liquid, a water-insoluble wax and an antiperspirant salt. Palinczar includes a minimum of 5% of the water-insoluble wax in the composition. In contrast, the present composition includes a wax in a maximum amount of about 4.5% by weight, because greater amounts of a wax provide a solid composition. The present composition is a liquid, a flowable semisolid or a nonflowable semisolid, having a viscosity in the range of from about 1000 cps (centipoise) to about 100,000 cps, that effectively resists phase separation by utilizing a low amount of a wax compound in the suspending wax composition.

Shin U.S. Pat. No. 4,937,069 discloses an anhydrous semi-solid antiperspirant composition that includes a minimum of 2% by weight fumed silica; a volatile emollient; a nonvolatile emollient; and a thickener. The composition disclosed by Shin is a cream or gel having a viscosity in the range of 100,000 to 8,800,000 cps (centipoise). The present composition is a liquid or a flowable semisolid including a maximum of less than 2% by weight finely-divided silica and demonstrating a viscosity in the range of from about 1,000 to about 100,000 cps.

Coopersmith U.S. Pat. No. 3,818,105 discloses that $C_{12}$ to $C_{14}$ isoparaffinic hydrocarbons, when combined with naphthenic materials, are useful in a wide range of cosmetic formulations for lubrication of the skin to achieve a quick spreading, non-greasy application with evaporation of the hydrocarbon after use without a greasy buildup. While the hydrocarbons disclosed in the Coopersmith patent lubricate the skin for better application of the cosmetic formula, the compositions of Coopersmith do not achieve the unexpected stability achieved in accordance with the present invention. Other compositions containing volatile hydrocarbons, such as those disclosed in Bolich U.S. Pat. No. 4,472,375, require polymeric water-soluble thickening agents, such as guar gum, to effectively stabilize the compositions.

Similarly, Spitzer et al., in U.S. Pat. No. 4,174,386, disclose an aerosol antiperspirant composition utilizing a volatile hydrocarbon including about three or four carbon atoms as the propellant. The present composition also can include a volatile hydrocarbon. However, the hydrocarbons used in the present invention include at least 10 carbon atoms and up to about 32 carbon atoms; act as a volatile carrier for the nonvolatile components of the composition; and then evaporate from the skin or hair after topical application of the composition. The stability of the anhydrous compositions of the present invention, achieved with a new and improved suspending agent including a finely-divided silica and a suspending wax composition, is unexpectedly superior to each of the above-identified prior compositions in regard to syneresis, cosmetic feel and degree of skin and clothing staining.

SUMMARY OF THE PRESENT INVENTION

The present invention is directed to a stable, anhydrous composition comprising a topically-active compound; a new and improved suspending agent comprising a finely-divided silica and a suspending wax composition; and a suitable volatile liquid carrier. The suspending wax composition comprises a natural or a synthetic wax, like castor wax; a volatile silica or a volatile hydrocarbon; and an aliphatic ester including at least 10 to about 32 carbon atoms.

Suspending wax compositions have been used in the paint industry as a suspending agent for pigments. Unexpectedly, it has been found that including a suspending wax composition, comprising a natural or synthetic wax, like castor wax; a volatile silicone or a volatile hydrocarbon; and an ester including at least 10 carbon atoms to about 32 carbon atoms, as an ingredient of the suspending agent in an anhydrous, topically-effective composition of the present invention eliminates the need for including the traditional organoclay suspending agents. The anhydrous topically-effective composition is a liquid, flowable semisolid or nonflowable semisolid composition that includes a particulate topically-active compound and that has a viscosity in the range of from about 1,000 cps (centipoise) to about 100,000 cps, and preferably from about 1,000 to about 40,000 cps. To achieve the full advantage of the present invention, the topically-effective composition has a viscosity in the range of from about 1,000 to about 5,000 cps. Compared to prior anhydrous liquid and semisolid compositions, the present topically-effective compositions effectively resist phase separation, or syneresis, over a prolonged storage period. Therefore, the topically-effective composition can be used without the need to shake the composition prior to each use in order to redisperse the composition ingredients. Surprisingly, it further was found that esthetic properties, like texture and consistency, or feel, of the antiperspirant composition are improved by masking, reducing, or eliminating the undesirable esthetic properties attributed to the traditional antiperspirant compounds, such as stickiness.

Another undesirable esthetic, or sensory, property improved by the present composition is grittiness. Previous compositions included relatively large amount of finely-divided silica, i.e. 2% or greater by weight, in order to sufficiently suspend the particulate ingredients present in the composition. However, the new and improved suspending agent of the present invention utilizes less than 2% by weight finely-divided silica, thereby effectively overcoming the problem of grittiness. Other undesirable esthetic properties reduced or eliminated by a composition of the present invention include oiliness and long-drying times caused by high percentages or traditional emollients and polyols; and whitening and staining of skin and clothing caused by organoclay suspending agents.

In addition, it has been found that the addition of a suspending emollient, such as a non-volatile silicone, an aromatic ester, an aliphatic ester, a high molecular weight polyol or an oil-soluble surfactant, to an anhydrous topically-effective composition of the present invention, further reduces or eliminates phase separation by enhancing the intermolecular bond formation, and therefore the suspending ability, of the finely-divided silica in the suspending agent. It should be understood that if an aromatic or aliphatic ester is included as the suspending emollient, the aromatic or aliphatic ester is added to the composition independently from the ester that is present in the suspending wax composition.

In one important embodiment of the present invention, the anhydrous, topically-effective composition of the present invention incorporates an astringent salt as the topically-active compound to form a stable and efficacious antiperspirant composition. In other embodiments of the present invention, the anhydrous, topically-effective composition incorporates topically effective drugs and medicaments; topical anesthetics; sunscreen agents; skin-soothing emollients and other topical cosmetic compounds; topical anti-inflammatories; and the like. The topically-active compound incorporated into the anhydrous compositions of the present invention can be soluble or insoluble in the volatile liquid carrier. However, the composition of the present invention is especially useful in the topical delivery of particulate, topically-active compounds in that are homogeneously dispersed throughout the stable, anhydrous composition by the new and improved suspending agent.

Accordingly, one important aspect of the present invention to provide an anhydrous, topically-effective composition including either a solubilized topically-active compound or an insoluble and suspended topically-active compound dispersed in a suitable, volatile liquid carrier by a new and improved suspending agent, such that the composition is a liquid, a flowable semisolid or a nonflowable semisolid composition having a viscosity in the range of from about 1,000 to about 100,000 cps, is stable and resists phase separation.

Another aspect of the present invention is to provide a stable, anhydrous, topically-effective composition including a topically-active compound, a suspending agent comprising a finely-divided silica and a suspending wax composition, wherein the topically-effective composition includes less than 2% by weight of the finely-divided silica; and a suitable volatile liquid carrier, wherein the composition has a viscosity in the range of from about 1,000 to about 100,000 cps.

Another aspect of the present invention is to provide an anhydrous, topically-effective composition that efficiently delivers a topically-active cosmetic or medicinal compound upon application to skin or hair.

Another aspect of the present invention is to provide an anhydrous, topically-effective composition useful as an antiperspirant and including a volatile silicone or volatile hydrocarbon compound, wherein the volatile hydrocarbon includes from about 10 to about 30 carbon atoms; an astringent salt; and a suspending agent comprising a finely-divided silica and a suspending wax composition, wherein the composition includes less than 2% by weight of the finely-divided silica.

Another aspect of the present invention is to provide an anhydrous, topically-effective composition that is not tacky, sticky or gritty during or after topical application, and that dries relatively quickly after topical application.

Another aspect of the present invention is to provide an anhydrous, topically-effective composition that is useful as an antiperspirant and that demonstrates reduced whitening and staining to the skin and to clothing after topical application.

It is also a further aspect of the present invention to provide an anhydrous antiperspirant composition that exhibits unexpectedly smooth topical application to the skin; effectively delivers the topically-active compound; and has superior sensory properties.

Other aspects of the present invention include providing an anhydrous, topically-effective composition for the administration of topically-active compounds, such as topically effective drugs and medicaments, topical anesthetics, sunscreen agents, skin-soothing emollients and other topical cosmetic compounds, topical anti-inflammatories and the like by incorporating the topically-active compound in an anhydrous composition comprising a new and improved suspending agent including a finely-divided silica and a suspending wax composition; and a volatile silicone, a volatile hydrocarbon or a combination thereof.

The above and other novel features and advantages of the present invention will become more apparent from the following detailed description of the preferred embodiments.

DETAILED DESCRIPTION OF THE INVENTION

A stable, anhydrous, topically-effective composition of the present invention includes a topically-active compound, such as an antiperspirant compound, like an astringent salt; a suspending agent comprising a finely-divided silica and a suspending wax composition; and a suitable volatile liquid carrier. The topically-effective composition is a liquid, a flowable semisolid or a nonflowable semisolid composition having a viscosity in the range of from about 1,000 to about 100,000 cps that is applied to the skin or hair. The liquid carrier then evaporates leaving the topically-active compound and other composition ingredients in contact with the skin or hair.

In accordance with an important feature of the present invention, the liquid or flowable semisolid composition effectively resists phase separation, or syneresis, over long storage periods because of the new and improved suspending agent included in the composition. Therefore, the topically-active composition is available for immediate application to the skin or hair without the need to shake or agitate the composition prior to use in order to redisperse the composition ingredients throughout the composition.

The topically-effective composition includes a suspending agent comprising a finely-divided silica and a suspending wax composition. The suspending wax composition comprises a natural or a synthetic wax, like castor wax; a volatile silicone, a volatile hydrocarbon including from about 10 to about 30 carbon atoms or a combination thereof; and an ester including at least 10 to about 32 carbon atoms. In accordance with an important feature of the present invention, the topically-effective composition includes less than 2% by weight of the finely-divided silica and about 4.5% or less by weight of the natural or synthetic wax.

More particularly, the stable, anhydrous, topically-effective composition of the present invention includes from about 0.01% to about 50% by weight of the total composition of a topically-active compound, such as an astringent salt having antiperspirant properties; a suspending agent comprising from about 0.1% to less than 2% by weight of the total composition of a finely-divided silica, as a thickening agent, and from about 1% to about 15% by weight of the total composition of a suspending wax composition; and from about 20% to about 98% by weight of the total composition of a suitable volatile liquid carrier.

The suspending wax composition included in the suspending agent utilized in the present invention comprises from about 5% to about 50%, and preferably from about 25% to about 35%, by weight of a natural wax or a synthetic wax, like castor wax; from about 0.1% to about 94.9%, and preferably from about 30% to about 50%, by weight of a volatile silicone, a volatile hydrocarbon including from about 10 to about 30 carbon atoms or a combination thereof; and from about 0.1% to about 94.9%, and preferably from about 25% to about 50%, by weight of an ester including at least 10 carbon atoms to about 32 carbon atoms. A suitable amount of the suspending wax composition is included in the topically-effective composition, in the range of about 1% to about 15% by weight, such that the amount of natural or synthetic wax in the topically-effective composition is about 4.5% or less by weight.

The suspending wax composition component of the suspending agent is essential to the efficacy of the present invention and, as will be discussed more fully hereinafter, the components of the suspending wax composition are preblended to form the suspending wax composition before admixing the suspending wax composition with the other ingredients of the composition of the present invention. It has been found that adding the individual components of the suspending wax composition to prepare a composition of the present invention does not effectively reduce or eliminate phase separation of the anhydrous, liquid or flowable semisolid composition.

Topically-Active Compounds

In accordance with an important feature of the present invention, a wide variety of topically-active compounds can be incorporated into a stable, anhydrous composition of the present invention. Such topically-active compositions include both cosmetic and medicinal compounds that act upon contact with the skin or hair. In accordance with another important feature of the present invention, the topically-active compound can be solubilized in the composition of the present invention or can be homogeneously dispersed throughout the composition as an insoluble, particulate material. In either case the anhydrous, topically-effective composition of the present invention is resistant to composition separation and effectively applies the topically-active compound to the skin or hair. In general, the topically-effective, anhydrous compositions of the present invention demonstrate essentially no phase separation if the topically-active compound is solubilized in the compositions. Furthermore, if the topically-active compound is insoluble in the composition, the anhydrous composition demonstrates essentially no phase separation if the insoluble topically-active compound has an average particle size less than about 1000$\mu$ (microns), and preferably less than about 100$\mu$, in diameter. To achieve the full advantage of the present invention, the topically-active compound has an average particle size of less than about 10$\mu$ in diameter.

The topically-active compound can be a cosmetically-active compound, a medically-active compound or any other compound that is useful upon application to the skin or hair. Such topically-active compounds include antiperspirants, antidandruff agents, antibacterial compounds, antifungal compounds, anti-inflammatory compounds, topical anesthetics, sunscreens and other cosmetic and medical topically-effective compounds.

Therefore, in accordance with an important feature of the present invention, the stable, anhydrous topically-effective composition can include any of the generally-known antiperspirant compounds such as finely-divided solid astringent salts like, but not limited to, aluminum chlorohydrate, aluminum chlorohydrox, zirconium chlorohydrate, and complexes of aluminum chlorohydrate with zirconyl chloride or zirconyl hydroxychloride, either in the presence or absence of an amino acid buffer such as glycine. In general, the amount of the antiperspirant compound, such as aluminum zirconium tetrachlorohydrex glycine for example, in the composition can range from about 0.01% to about 50%, and preferably from about 0.1% to about 30%, by weight of the total composition. To achieve the full advantage of the present invention, the antiperspirant compound is present in the range of from about 5% to about 25% by weight.

In addition to antiperspirant compounds, other topically-active compounds can be included in the anhydrous compositions of the present invention in an amount sufficient to perform their intended function. For example, zinc oxide, titanium dioxide or similar compounds can be included if the composition is intended to be a sunscreen. Similarly, topically-active drugs, like antifungal compounds; antibacterial compounds; anti-inflammatory compounds; topical anesthetics; skin rash, skin disease and dermatitis medications; and anti-itch and irritation-reducing compounds can be included in the compositions of the present invention. For example, analgesics such as benzocaine, dyclonine hydrochloride, aloe vera and the like; anesthetics such as butamben picrate, lidocaine hydrochloride, xylocaine and the like; antibacterials and antiseptics, such as povidone-iodine, polymyxin b sulfate-bacitracin, zinc-neomycin sulfate-hydrocortisone, chloramphenicol, methylbenzethonium chloride, and erythromycin and the like; antiparasitics, such as lindane; deodorants, such as chlorophyllin copper complex, aluminum chloride, aluminum chloride hexahydrate, and methylbenzethonium chloride; essentially all dermatologicals, like acne preparations, such as benzoyl peroxide, erythromycin-benzoyl peroxide, clindamycin phosphate, 5,7-dichloro-8-hydroxyquinoline, and the like; anti-inflammatory agents, such as alclometasone dipropionate, betamethasone valerate, and the like; burn relief ointments, such as o-amino-p-toluenesulfonamide monoacetate and the like; depigmenting agents, such as monobenzone; dermatitis relief agents, such as the active steroid amcinonide, diflorasone diacetate, hydrocortisone, and the like; diaper rash relief agents, such as methylbenzethonium chloride and the like; emollients and moisturizers, such as mineral oil, PEG-4 dilaurate, lanolin oil, petrolatum, mineral wax and the like; fungicides, such as butocouazole nitrate, haloprogin, clotrimazole, and the like; herpes treatment drugs, such as 9-[(2-hydroxyethoxy)methyl]guanine; pruritic medications, such as alclometasone dipropionate, betamethasone valerate, isopropyl myristate MSD, and the like; psoriasis, seborrhea and scabicide agents, such as anthralin, methoxsalen, coal tar and the like; sunscreens, such as octyl p-(dimethylamino)benzoate, octyl methoxycinnamate, oxybenzone and the like; steroids, such as 2-(acetyloxy)-9-fluoro-1',2',3',4'-tetrahydro-11-hydroxypregna-1,4-dieno[16,17-b]naphthalene-3,20-dione and 21-chloro-9-fluoro-1',2',3',4'-tetrahydro-11b-hydroxypregna-1,4-dieno[16z,17-b]naphthalene-3,20-dione. Any other medication capable of topical administration also can be incorporated in an anhydrous composition of the present invention in an amount sufficient to perform its intended function.

Volatile Liquid Carrier

The topically-active compound of the composition is dispersed into a non-aqueous, volatile liquid carrier, such as a volatile silicone or a volatile hydrocarbon. It should be understood that although the composition of the present invention is preferably an anhydrous composition, it has been found that amounts of water up to about 2% by weight of the composition can be present without adversely affecting the composition. The water can be included intentionally or inadvertently as an ingredient in a component of the composition. However, to avoid a sticky feeling after application of the topically-effective composition to the skin, the amount of water should be present at less than 2% by weight, and to achieve the full advantage of the present invention, at less than about 1% by weight of the composition. After topical application of a composition of the present invention, the non-aqueous, volatile liquid carrier facilitates the rapid absorption of the topically-active compound onto the skin, thereby eliminating the wet feeling of the carrier vehicle. The volatile liquid carrier then slowly evaporates, leaving the topically-active compound in contact with the skin.

Suitable non-aqueous volatile liquid carriers useful in the composition of the present invention include the volatile, low molecular weight polydimethylsiloxane compounds. The volatile, low molecular weight polydimethylsiloxane compound can be either a linear or a cyclic polydimethylsiloxane compound, as long as the polydimethylsiloxane compound has sufficient volatility to volatilize from the skin after topical application of the composition onto the skin. Preferably the polydimethylsiloxane is a cyclic siloxane, like cyclomethicone. The volatile silicones, such as cyclomethicone, feel very rich as they are applied to the skin, but then evaporate relatively quickly to leave only the non-volatile components of the composition on the skin. In general, volatile polydimethylsiloxane compounds useful in the compositions of the present invention include polydimethylsiloxane compounds having a viscosity in the range of from about 0.5 cs (centistokes) to about 10 cs. The preferred volatile polydimethylsiloxanes have a viscosity in the range of from about 2 cs to about 6 cs.

The cyclic, low molecular weight, volatile polydimethylsiloxanes, designated in the *CTFA Cosmetic Ingredient Dictionary.* 3rd. Edition (1982) as cyclomethicones, are the preferred siloxanes used in a composition of the present invention. To achieve the full advantage of the present invention, a cyclomethicone used in a composition of the present invention is a low viscosity, low molecular weight, water-insoluble cyclic compound having an average of about 3 to about 6 —[O-Si(CH₃)₂]— repeating group units per molecule; boil at atmospheric pressure in a range of from about 150° C. to about 250° C.; and have viscosities at 25° C. of from about 2 to about 6 centistokes. The polydimethyl cyclosiloxanes having an average of about 4 to about 5 repeating units per molecule, i.e., the tetramer and pentamer, are especially preferred. Suitable cyclomethicones are available commercially under the tradenames SILICONE 344 FLUID and SILICONE 345 FLUID from Dow Corning Corporation, Midland, Mich., and SILICONE SF-1173 and SILICONE SF-1202 from General Electric, Waterford, N.Y., the tetramer being listed first in each instance.

An example of a linear, low molecular weight, volatile polydimethylsiloxane compound that is useful in the composition and method of the present invention is the compound named in the *CTFA Dictionary* as hexamethyldisiloxane, available commercially under the tradename DOW CORNING 200 FLUID from Dow Corning Corp., Midland, Mich. Hexamethyldisiloxane has a viscosity of 0.65 cs, is highly volatile, is non-greasy, and provides lubrication for topical application to the composition of the present invention to the skin. Other linear polydimethylsiloxanes, such as decamethyltetrasiloxane, having a boiling point of about 195° and a viscosity of 1.5 cs; octamethyltrisiloxane; and dodecamethylpentasiloxane, also have sufficient volatility to be useful in the composition of the present invention. In general, it has been found that a linear, low molecular weight volatile polydimethylsiloxane compound having a viscosity at 25° C. and atmospheric pressure in the range of from about 0.5 cs to about 5 cs, and a boiling point at atmospheric pressure ranging from about 100° C. to about 250° C., are preferred for use in the composition and method of the present invention.

The volatile liquid carrier included in a composition of the present invention also can be a volatile hydrocarbon, such as a hydrocarbon including from about 10 to about 30 carbon atoms, that has sufficient volatility to slowly volatilize from the skin or hair after application of the topically-effective composition. The volatile hydrocarbons provide essentially the same benefits as the volatile silicones, such as lubrication and a rich feel during application.

The preferred volatile hydrocarbon is an aliphatic hydrocarbon including from about 12 to about 24 carbon atoms, and having a boiling point in the range of from about 100° C. to about 300° C. Exemplary volatile hydrocarbons are depicted in general structural formula (I), wherein n ranges from 2 to 5.

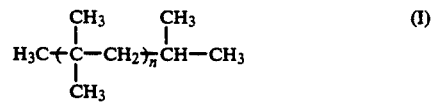

Specific examples of volatile hydrocarbons useful in the anhydrous composition of the present invention include, but are not limited to, the commercially-available compounds PERMETHYL 99A and PERMETHYL 101A, corresponding to compounds of general structure (I) wherein n is 2 or 3, respectively, available from Permethyl Corporation, Frazer, Pa. A volatile hydrocarbon is useful in the composition of the present invention either alone, in combination with another volatile hydrocarbon, or in combination with a volatile silicone.

Suspending Agent

The suspending agent of the present composition comprises: (i) a finely-divided silica, and (ii) a suspending wax composition. The finely-divided silica used in the suspending agent of the present invention helps suspend the particulate topically-active compound in the volatile liquid carrier; aids in absorbing the volatile liquid carrier; and aids in reducing the preventing composition separation. The finely-divided silica is present in a composition of the present invention in the range of from about 0.1% to less than 2%, and preferably in the range of from about 0.1% to about 1.5%., by weight of the composition to provide a sufficient composition consistency suitable for use in a roll-on topically-effective product. To achieve the full advantage of the present invention, the finely-divided silica is present in the range of from about 0.2% to about 1.5% by weight of the composition.

Amounts of finely-divided silica in the range of from about 1.5% up to less than 2% by weight of the composition can be used to provide a topically-effective composition having the consistency of a flowable semisolid that demonstrates thixotropic rheological properties, if the amount of a suspending wax composition included in the composition is near its lower limit, such as from about 1% to about 5% by weight of the composition. Such flowable semisolids exhibit a viscosity in the range of from about 5,000 to about 40,000 cps. Including amounts of finely-divided silica in excess of about 2% by weight provides a composition that has too stiff of a consistency and that has a gritty, and therefore, unpleasant and unacceptable, consistency and feel.

If the amount of the suspending wax composition in the topically-active composition is above about 5% by weight, and if the amount of finely-divided silica is in the range of about 1.5% to less than 2% by weight, the topically-effective composition is a nonflowable semisolid having a viscosity in the range of from about 40,000 to about 100,000 cps. At lower amounts of suspending wax composition and finely-divided silica, the topically-effective composition is a liquid having a viscosity of from about 1,000 to about 5,000 cps.

In accordance with an important feature of the present invention, the finely-divided silica should have an average particle size in the range of from about $0.001\mu$ (microns) to about $0.05\mu$, and preferably in the range of from about $0.005\mu$ to about $0.03\mu$. To achieve the full advantage of the present invention, the finely-divided silica has an average particle size in the range of from about $0.01\mu$ to about $0.02\mu$. A suitable finely-divided silica is fumed silica having an average particle size ranging from about $0.014\mu$ to about $0.016\mu$, and available from Cabot Corp., Tuscola, Fla. under the tradename CAB-O-SIL M-5, or from DeGussa Corp., Teterboro, N.J. under the tradename AEROSOL COLLOIDAL SILICA. It also was found that shearing the finely-divided silica prior to adding the silica to the volatile liquid carrier vehicle of the present invention further enhanced intermolecular silica bond formation, thereby further contributing to reduced phase separation.

The stable, anhydrous topically-effective compositions of the present invention also include from about 1% to about 15%, and preferably from about 1.5% to about 10%, by weight of the composition of a suspending wax composition as a component of the suspending agent. To achieve the full advantage of the present invention, the topically-effective composition includes from about 1.5% to about 7% by weight of the suspending wax composition. The suspending wax composition includes from about 5% to about 50%, and preferably from about 25% to about 35%, by weight of a natural or a synthetic wax; from about 0.1% to about 94.9%, and preferably from about 30% to about 50%, by weight of a volatile silicone, a volatile hydrocarbon including from about 10 to about 30 carbon atoms or a combination thereof; and from about 0.1% to about 94.9%, and preferably from about 25% to about 50%, by weight of an ester including at least 10 to about 32 carbon atoms. In accordance with an important feature of the present invention, the suspending wax composition is included in a topically-effective composition of the present invention in an amount such that the topically-effective composition includes about 4.5% or less by weight of the natural or synthetic wax. In accordance with another important feature of the present invention, the suspending wax composition is included in a topically-effective composition of the present invention as a preblend, as opposed to individually adding the three separate components of the suspending wax composition to the topically-effective composition.

The suspending wax composition was prepared, for example, by dispersing about 30 parts by weight of a wax, like castor wax, in a mixture comprising about 16.5 parts by weight of an ester, like dioctyl adipate, and about 18.5 parts by weight cyclomethicone. The resulting dispersion (phase A) was heated to a temperature above the melting point of the castor wax, like to about 190° F. (87.8° C.). A room temperature mixture (phase B) comprising about 16.5 parts by weight dioctyl adipate and about 18.5 parts by weight cyclomethicone was added to the molten phase A, under continuous high shear stirring, as a thin stream. The addition of the room temperature phase B to molten phase A as a thin stream shock cools the resulting mixture down to a temperature of about 150° F. (65.6° C.) within one minute. The rapid temperature drop seeds the mixture, and with continuous high shear, a paste. like suspending wax composition useful in a composition of the present invention is prepared.

The wax used in the suspending wax composition can be a natural wax or synthetic wax, provided the wax is soluble in a hydrophobic carrier, such as a volatile silicone, above the melting point of the wax. In addition, the wax should be heat stable and have a sufficiently high melting point such that the wax precipitates from the hydrophobic carrier as the hydrophobic carrier cools. The precipitated wax therefore forms a matrix that helps suspend the insoluble composition ingredients in the volatile liquid carrier.

Accordingly, the wax provides a degree of rigidity to the suspending wax composition. It has been found that specific waxes differ in performance based upon the melting point and the degree of crystallinity of the wax. Therefore, the amount of wax included in the suspending wax composition, and ultimately in the topically-effective composition, is related to the physical properties of the wax. Consequently, a wax included in the suspending wax composition has a melting point of at least 150° F. (65.6° C.), and preferably at least 170° F. (76.7° C.). However, a wax having a melting point lower than 150° C. (65.6° C.), such as down to about 100° F. (37.8° ), can be included as a component of the wax, as long as this low melting wax is used in combination with a wax having a melting point of at least about 150° F. (65.6° C.).

Therefore, waxes having a melting point of at least 150° F. (65.6° C.) and that improve the rigidity of the suspending wax composition include, but are not limited to, castor wax, beeswax, carnauba wax, ozokerite wax, candellila wax and montan wax. To achieve the full advantage of the present invention, castor wax, comprising glyceryl tri(2-hydroxystearate), is used as the wax. Castor wax is a hard, high-melting wax that demonstrates good heat stability; is compatible with the majority of other waxes; and is an excellent substitute for the expensive, high-melting natural waxes. Other suitable waxes include, but are not limited to, polyethylene wax, stearic acid, palmitic acid, hydrogenated fats, microcrystalline wax, lanolin wax, polyoxyethylene, bayberry wax, Japan wax, jojoba wax, mink wax, ouricury wax, rice bran wax, shellac wax and combinations thereof.

Although a hard wax having a melting point above about 170° F. (76.7° C.) is the preferred wax, a wax that melts above about 150° F. (65.6° C.) and below about 170° F. (76.7° C.) also can be used in the suspending wax composition. However, a greater amount of the wax that melts about 150° F. (65.6° C.) may be needed to achieve the same results as a wax that melts above about 170° F. (76.7° C.). In addition, a soft wax that melts below about 150° F. (65.6° C.) also can be used as a wax in the suspending wax composition as long as a sufficient amount of a wax melting above about 150° F. (65.6° C.) also is included in the suspending wax composition. Suitable soft waxes that can be used in conjunction with a hard wax include, for example, but are not limited to, paraffin waxes, cetyl alcohol, stearyl alcohol and spermaceti wax.

Furthermore, it should be understood that the proportion of the wax and the ester in the suspending wax composition is varied to achieve the desired consistency of the suspending wax composition depending upon the identity of the particular wax and the particular ester. In general however, the particular identity of the wax is not critical as long as the wax provides a smooth and creamy sensory feeling and can be incorporated in to the paste-like suspending wax composition, as described above.

The volatile silicone or volatile hydrocarbon included in the suspending wax composition is selected from the identical volatile silicones and volatile hydrocarbons included in the anhydrous, topically-effective composition of the present invention as the volatile liquid carrier. For example, volatile silicones that can be included in the suspending wax composition include the low molecular weight polydimethylsiloxane compounds, such as the cyclic polydimethylsiloxane tetramer and the cyclic polydimethylsiloxane pentamer, available commercially under the tradenames SILICONE 344 FLUID and SILICONE 345 LIQUID, respectively, from Dow Corning Corp., Midland, Mich., and SF-1173 and SF-1202, respectively, from General Electric, Waterford, N.Y. A suitable volatile hydrocarbon can be substituted for, or used in conjunction with, the volatile silicone. Volatile hydrocarbons having from about 10 to about 30 carbon atoms, and a boiling point in the range of from about 100° C. to about 300° C., such as, for example, PERMETHYL 99A available from Permethyl Corp., Frazer, Pa., are suitable for use in the suspending wax composition.

An ester also is included in the suspending wax composition. Although the identity of the specific ester, or combination of esters, is not especially critical, it has been found that a suitable ester includes at least 10 carbon atoms, and preferably the ester includes from about 10 to about 32 carbon atoms. For example, suitable esters include those comprising an aliphatic alcohol or an aliphatic polyol including from about eight to about twenty carbon atoms and an aliphatic or aromatic carboxylic acid including from two to about twelve carbon atoms, or conversely, an aliphatic alcohol or polyol including from two to about twelve carbon atoms with an aliphatic or aromatic carboxylic acid including from about eight to about twenty carbon atoms. A suitable ester is either straight-chained or branched; and is a liquid at room temperature, having a melting point at about 22° C. or lower. Preferably, the ester has a molecular weight of less than about 500, provides emollient properties, and is soluble in a hydrophobic carrier. Suitable esters therefore include, for example, but are not limited to:

a) aliphatic monohydric alcohol esters, including but not limited to:
myristyl propionate,
isopropyl isostearate,
isopropyl myristate,
isopropyl palmitate,
cetyl acetate,
cetyl propionate,
cetyl stearate,
isodecyl neopentanoate,
cetyl octanoate,
isocetyl stearate;

b) aliphatic di- and tri-esters of polycarboxylic acids, including but not limited to:
diisopropyl adipate,
diisostearyl fumarate,
dioctyl adipate, and
triisostearyl citrate;

c) aliphatic polyhydric alcohol esters, including but not limited to:
propylene glycol dipelargonate,
propylene glycol laurate,
glyceryl isostearate, and
neopentylglycol dioctanoate;

d) aliphatic alkoxylated esters, including but not limited to:
propylene glycol ceteth-3-acetate, and
propylene glycol isoceteth-3-acetate; and e) aliphatic esters of aromatic acids, including but not limited to:
$C_{12}$–$C_{15}$ alcohol esters of benzoic acid,
laureth-2 benzoate,
octyl salicylate,
sucrose benzoate, and
dioctyl phthalate.

Numerous other suitable esters are listed in the *CTFA Cosmetic Ingredient Handbook, First Ed.* (1988) at pages 24 through 26. Preferred esters include dioctyl adipate, $C_{12-15}$ alcohol benzoates, noepentyl glycol dioctanoate, isodecyl neopentanoate, cetyl stearate and isocetyl stearate. To achieve the full advantage of the present invention, dioctyl adipate is used as the aliphatic ester in the suspending wax composition. It should be understood that the straight chain esters (e.g. cetyl stearate) are preferred because straight chain esters are faster drying than the corresponding branched esters (e.g. isocetyl stearate).

Unexpectedly, it was found that including a sufficient amount of the suspending wax composition in an anhydrous, topically-effective composition of the present invention provides a stable composition that resists phase separation, and that eliminates the need to include an organoclay suspending agent. However, the suspending wax composition cannot introduce more than about 4.5% by weight natural or synthetic wax into the topically-effective composition because the composition consistency becomes too stiff and hard.

The suspending wax composition effectively helps disperse and suspend the topically-active compound thereby requiring a low amount of finely-divided silica, i.e. below 2%, and often below 1%, by weight, to provide an essentially syneresis-free, topically-effective composition having a viscosity in the range of from about 1,000 to about 100,000 cps, and preferably in the range of from about 1,000 to about 40,000 cps. To achieve the full advantage of the present invention the topically-effective composition has a viscosity in the range of from about 1,000 to about 5,000 cps. Accordingly, the composition provides an added advantage in overcoming the gritty and scratchy feel of a topically-effective composition that includes a finely-divided silica in an amount of 2% by weight or greater. Consequently, the topically-effective composition is suitable as a cosmetic roll-on product that does not require shaking prior to use; that reduces whitening and nonstaining, and is non-oily after topical application; that dries quickly after topical application; and that exhibits improved efficacy and sensory properties.

To demonstrate the effect of the finely-divided silica and the suspending wax composition on the viscosity of composition of the present invention, several compositions including varying amounts of finely-divided silica and suspending wax composition were prepared, then the viscosity of each composition was determined by standard procedures. The viscosities of the compositions are tabulated below in TABLE I. The data in TABLE I shows that the viscosity of the composition can be varied by adjusting the absolute and the relative amounts of the finely-divided silica and the suspending wax composition in the topically-effective composition. It should be noted however that if the amount of natural or synthetic wax in the topically-effective composition exceeds about 4.5% by total weight of the composition, the viscosity is too high and the composition is too hard, thereby having an unsuitable consistency to perform as a roll-on product. TABLE I illustrates that the amount of finely-divided silica and suspending wax composition in the topically-effective semisolid can be varied to provide either a liquid composition (Composition F), a flowable semisolid composition (Compositions A and B), or a nonflowable semisolid composition (Compositions C, D and E). Each composition A through F exhibited essentially no syneresis after extended storage periods, and each composition was easy to apply and exhibited excellent esthetic properties after application.

TABLE I

VISCOSITY OF TOPICALLY-EFFECTIVE COMPOSITIONS

| Composition[1] | % Finely-Divided Silica[2] | % Suspending Wax Composition[3] | Vis. (24 h)[4] | Vis. (7 day)[5] |
|---|---|---|---|---|
| A | 1.9 (by weight) | 3 (by weight) | 23,600 | 26,000 |
| B | 1.9 | 5 | 40,000 | 43,000 |
| C | 1.9 | 10 | 66,000 | 71,000 |
| D | 1.9 | 13 | 76,000 | 84,000 |
| E | 1.9 | 15 | 84,000 | 90,000 |
| F | 0.8 | 2.65 | 4,700 | 4,500 |

[1] Each composition also includes 22% by weight aluminum zirconium tetrachlorohydrex glycinate as a topically-active compound; and includes cyclomethicone (DOW CORNING 344 FLUID, Dow Corning Corp., Midland, MI.) as the balance of the composition;
[2] CAB-O-SIL, Cabot Corporation, Tuscola, IL;
[3] The suspending wax composition includes 30% castor wax, 33% dioctyl adipate and 37% cyclomethicone, by weight;
[4] Viscosity after 24 hours in cps; and
[5] Viscosity after 7 days in cps.

Optional Ingredients

In addition to the essential ingredients, one or more optional suspending emollients can be included in a topically-effective composition of the present invention to further aid in the reduction and elimination of phase separation, whitening, and staining; and to further impart favorable sensory properties to the composition. Suitable optional suspending emollients include, but are not limited to a nonvolatile silicone oil, a high molecular weight polyol, an oil-soluble surfactant, an aromatic ester, an aliphatic ester and similar organic compounds. For example, a composition of the present invention can include a compatible skin-soothing suspending emollient such as a benzoate ester of an alcohol having from about 8 to about 30 carbon atoms, like a $C_{12-15}$ alcohol benzoate aromatic ester; a nonvolatile dimethylsilicone fluid or a nonvolatile diphenylsilicone fluid; or like compounds. The suspending emollient, or combination of suspending emollients, can be present in the topically-effective composition of the present invention in an amount ranging from 0% to about 30%, and preferably from about 5% to about 20%, by weight of the composition. It should be understood that if an aliphatic ester is included in the composition as an optional suspending emollient, then the aliphatic ester is added in addition to, and independent of, the aliphatic ester present in the composition as a component of the suspending wax composition.

The nonvolatile silicone oil suspending emollient can be a nonvolatile dimethylpolysiloxane fluid or a nonvolatile diphenylsiloxane fluid. A preferred nonvolatile silicone is a dimethylsiloxane fluid listed in the *CTFA Dictionary* as a dimethicone and has a viscosity of at least about 10 centistokes.

The optional incorporation of a high molecular weight polyol or an oil-soluble surfactant into a topically-effective composition of the present invention also aids in the reduction or elimination of composition phase separation, the reduction of whitening and staining after composition application and the enhancement of the sensory properties of the composition. High molecular weight polyols or oil-soluble surfactants that can be included in a composition of the present invention include, but are not limited to, polysorbate 60, polypropylene glycol, decyl pyrrolidone, nonoxynol-2, and similar nonionic surfactants and polyols. Yet another optional suspending emollient that can be included in a composition of the present invention is an aromatic ester or an aliphatic ester. Suitable aromatic esters include, but are not limited to, laureth-3 benzoate, laureth-2 benzoate, $C_{12}$–$C_{15}$ alcohol benzoates, dioctyl phthalate and sucrose benzoate. Suitable aliphatic esters include those above-described esters that can be included in the suspending wax composition, such as dioctyl adipate, isocetyl stearate, cetyl stearate, neopentyl glycol dioctanoate and similar aliphatic esters.

Furthermore, minor amounts of emollients such as fatty esters, fatty alcohols, mineral oil, polyether siloxane copolymers and the like, also can be included in a topically-effective composition of the present invention. Usually, such optional emollients are included in amounts ranging from 0% to about 10% by weight of the topically-effective composition. Examples of optional emollients include, but are not limited to PPG-15 stearyl ether, PPG-10 cetyl ether, steareth-10, oleth-8 and PPG-4 lauryl ether.

In addition to the ingredients listed above, the anhydrous, topically-effective compositions of the present invention also can include other optional ingredients that are conventionally included in topical cosmetic and medicinal compositions. For example, fragrances can be incorporated into the anhydrous, topically-effective composition in an amount of from 0% to about 5% based on the total weight of the composition. The composition of the present invention, when applied to skin, therefore fixes a substantive fragrance film on the skin that resists moisture, but that can be removed by washing. Other optional ingredients that can be included in the anhydrous composition of the present invention include, but are not limited to, drying agents, like talc or DRY FLO (aluminum starch octenylsuccinate); preservatives; and dyes. Generally, such optional ingredients are present in a composition of the present invention in an amount of about 10% or less by weight. In addition, although the necessity of including an organoclay is virtually eliminated by the use of the new and improved suspending agent, an organoclay can be included in a composition of the present invention as an additional suspending agent in an amount of up to 20% by weight of the composition. An organoclay is especially helpful as an anticaking agent to maintain a particulate topically-effective compound homogeneously dispersed throughout the composition. An exemplary organoclay is a quaternized three-layer clay exfoliated with a polar solvent, like a quaternized montmorillonite clay exfoliated with propylene carbonate.

The following specific examples are illustrative of the anhydrous, topically-effective compositions of the present invention. However, it should be understood that the present invention is not limited to the specific examples set forth below. By varying the proportions and the type of each of the essential ingredients within the above-indicated ranges, a composition of the present invention can be prepared in a liquid, a flowable semisolid or a nonflowable semisolid form. In the following examples, all amounts of the various ingredients are expressed by weight percentages unless otherwise specified. In each of the following examples, the suspending wax composition includes about 30% castor wax, about 37% cyclomethicone, and about 33% dioctyl adipate; and is a paste-like, gel material.

EXAMPLE 1

| Ingredient | % (by weight) |
| --- | --- |
| Fumed silica[1] | 1.5 |
| Cyclomethicone[2] | 73.5 |
| Aluminum Zirconium Tetrachlorohydrex Glycinate[3] | 22.0 |
| Suspending Wax Composition[4] | 3.0 |

[1] CAB-O-SIL, Cabot Corporation, Tuscola, IL.
[2] DOW CORNING 344 FLUID, Dow Corning Corp., Midland, MI.
[3] Wickenol CPS 370, Wickhen Products, Huguenot, NY.
[4] The suspending wax composition contributes 0.9% castor wax, 1.0% dioctyl adipate and 1.1% cyclomethicone to the total weight of the composition. The suspending wax composition was prepared by the method described above.

Procedure

The fumed silica was dispersed in the volatile liquid cyclomethicone, and the mixture was thoroughly blended until homogeneous. The aluminum chlorohydrate and the suspending wax composition then were added to the silica-silicone mixture, and the resulting mixture was charged through a colloid mill for at least two minutes until homogeneous. The resulting composition was a flowable semisolid having rheological physical properties suitable for use as a roll-on antiperspirant product, such as a viscosity of about 20,000 cps. When topically-applied to the skin, the antiperspirant product was dry to opposed to oily or sticky; and the antiperspirant product exhibited excellent esthetic properties. After an approximately one year aging period at 27° C., the antiperspirant product of Example 1 showed negligible phase separation.

EXAMPLE 2

| Ingredient | % (by weight) |
| --- | --- |
| Fumed silica[1] | 1.5 |
| Dimethicone[5] | 20.0 |
| Cyclomethicone[2] | 53.5 |
| Aluminum Zirconium Tetrachlorohydrex Glycinate[3] | 22.0 |
| Suspending Wax Composition[4] | 3.0 |

[5] SILICONE SF-9650, General Electric, Waterford, NY. A non-volatile dimethylpolysiloxane fluid included as an optional suspending emollient.

Procedure

The fumed silica was dispersed in the dimethicone and cyclomethicone, and the mixture was thoroughly blended until homogeneous. The aluminum chlorohydrate and suspending wax composition then were added to the silica-silicone mixture, and the resulting mixture was mixed at a high shear in a colloid mill until homogeneous. The resulting liquid composition possessed suitable physical properties, like a viscosity of about 4,000 cps, for use as a roll-on antiperspirant product. When topically applied to the skin, the antiperspirant product was dry, as opposed to oily or sticky, and the antiperspirant product exhibited excellent esthetic properties. The antiperspirant product showed negligible phase separation after a greater than one year aging period at 27° C. The viscosity of the composition decreased over this period.

EXAMPLE 3

| Ingredient | % (by weight) |
| --- | --- |
| Fumed silica[1] | 1.5 |
| C$_{12}$–C$_{15}$ Alcohol Benzoate[6] | 10.0 |
| Cyclomethicone[2] | 63.5 |
| Aluminum Zirconium Tetrachlorohydrex Glycinate[3] | 22.0 |
| Suspending Wax Composition[4] | 3.0 |

[6] FINSOLV TN, Finetex, Inc., Elmwood Park, NY. An aromatic ester included as an optional suspending emollient.

Procedure

The fumed silica was dispersed in the C$_{12}$–C$_{15}$ alcohol benzoate and the cyclomethicone, and the mixture was thoroughly blended until homogeneous. The aluminum chlorohydrate and the suspending wax composition then were added to the silica-silicone-benzoate mixture, and the resulting mixture was charged through a colloid mill for at least 2 minutes. The resulting liquid composition possessed physical properties suitable for use as a roll-on antiperspirant product. When topically-applied to the skin, the resulting antiperspirant product was dry, as opposed to oily or sticky, and the antiperspirant product exhibited excellent esthetic properties. The antiperspirant product showed negligible phase separation after an approximately 1 year aging period at 27° C.

EXAMPLE 4

| Ingredient | % (by weight) |
| --- | --- |
| Fumed silica[1] | 1.50 |
| Polysorbate 60[7] | 0.24 |
| C$_{12}$–C$_{15}$ Alcohol Benzoate[6] | 10.00 |
| Cyclomethicone[2] | 63.26 |
| Aluminum Zirconium Tetrachlorohydrex Glycinate[3] | 22.00 |
| Suspending Wax Composition[4] | 3.00 |

[7] TWEEN 60, ICI Americas, Wilmington DE. An oil-soluble surfactant included as an optional suspending emollient.

Procedure

The fumed silica was dispersed in a blend of polysorbate 60, the C$_{12}$–C$_{15}$ alcohol benzoate and the cyclomethicone, then the mixture was thoroughly blended until homogeneous. The aluminum chlorohydrate and the suspending wax composition were added to the homogeneous mixture, and the resulting mixture was charged through a colloid mill for at least 2 minutes until homogeneous. The resulting liquid composition possessed physical properties suitable for use as a roll-on antiperspirant product. When topically-applied to the skin, the antiperspirant product was dry, as opposed to oily or sticky, and the antiperspirant product exhibited excellent esthetic properties. The antiperspirant product showed essentially no phase separation after an approximately 1 year aging period at 27° C.

EXAMPLE 5

| Ingredient | % (by weight) |
|---|---|
| Fumed silica[1] | 1.50 |
| Dimethicone[5] | 15.00 |
| $C_{12}$–$C_{15}$ Alcohol Benzoate[6] | 5.00 |
| Cyclomethicone[2] | 53.73 |
| Polysorbate 60[7] | 0.12 |
| Aluminum Zirconium Tetrachlorohydrex Glycinate[3] | 22.00 |
| Suspending Wax Composition[4] | 2.65 |

Procedure

The fumed silica, dimethicone, and $C_{12}$–$C_{15}$ alcohol benzoate were thoroughly admixed until the fumed silica was uniformly dispersed. The cyclomethicone and the polysorbate 60 were added to the mixture, and the resulting mixture then was transferred to a colloid mill and mixed for 2 minutes until the mixture was homogeneous. The aluminum chlorohydrate then was added, and the composition was mixed until the aluminum chlorohydrate was completely dispersed. The suspending wax composition then was added to the mixture, and the resulting mixture was mixed until homogeneous. The homogeneous mixture then was returned to the colloid mill and mixed for at least 3 minutes. The resulting composition possessed physical properties suitable for use as a roll-on antiperspirant product. When topically-applied to the skin, the antiperspirant product was dry, as opposed to oily or sticky, and the antiperspirant product exhibited excellent esthetic properties. The antiperspirant product showed no phase separation after a greater than one year aging period at 27° C.

EXAMPLE 6

| Ingredient | % (by weight) |
|---|---|
| Cyclomethicone[2] | 47.55 |
| Aluminum Zirconium Tetrachlorohydrex Glycinate[3] | 22.00 |
| Fumed silica[1] | 1.50 |
| Suspending Wax Composition[8] | 2.65 |
| Dimethicone[5] | 20.00 |
| Hydrophobic Starch Derivative[9] | 1.00 |
| Dioctyl Adipate[10] | 3.50 |
| Fragrance | 0.30 |
| Starch/Dextrin Fragrance | 1.50 |

[8] The suspending wax composition contributes 0.80% castor wax, 0.98% dioctyl adipate and 0.87% cyclomethicone to the total weight of the composition.
[9] DRY FLO, National Starch and Chemical Co., Bridgewater, NJ., aluminum starch octenylsuccinate.
[10] WICKENOL 158, Wickhen Products, Huguenot, NY. An aliphatic ester included as an optional suspending agent.

Procedure

The fumed silica, dimethicone and cyclomethicone were thoroughly admixed until the fumed silica was uniformly dispersed. The mixture then was transferred to a colloid mill and mixed for at least 2 minutes, or until the mixture was homogeneous. The aluminum chlorohydrate and the hydrophobic starch derivative then were added to the mixture, and the resulting mixture was blended until both additives were completely dispersed. The suspending wax composition then was added to the mixture, and the resulting mixture was mixed until homogeneous. A premix of the dioctyl adipate and the fragrances then was added to the homogeneous mixture. The resulting mixture was returned to the colloid mill and mixed for at least 3 minutes. The final liquid composition possessed physical properties suitable for use as a roll-on antiperspirant product. When topically-applied to the skin, the antiperspirant product was dry, as opposed to oily or sticky, and the antiperspirant product exhibited exceptional esthetic properties. The antiperspirant product showed negligible phase separation after a greater than one year aging period at 27° C.

EXAMPLE 7

| Ingredient | % (by weight) |
|---|---|
| Cyclomethicone[2] | 38.13 |
| Aluminum Zirconium Tetrachlorohydrex Glycinate[3] | 22.00 |
| Fumed silica[1] | 0.80 |
| Suspending Wax Composition[10] | 2.65 |
| Polysorbate 60[7] | 0.12 |
| Dimethicone[5] | 10.00 |
| $C_{12}$–$C_{15}$ Alcohol Benzoate[6] | 10.00 |
| Quaternium-18 Hectorite in cyclomethicone[11] | 10.00 |
| Hydrophobic Starch Derivative[8] | 1.00 |
| Dioctyl Adipate[9] | 3.50 |
| Fragrance | 0.30 |
| Starch/Dextrin Fragrance | 1.50 |

[11] BENTONE GEL VS/5 PC, NL Chemicals, Hightstown, NJ., including 75% (by weight) volatile silicone, 5% propylene carbonate and 20% Quaternium-18 hectorite.

Procedure

The fumed silica, dimethicone, cyclomethicone, polysorbate 60 and $C_{12}$–$C_{15}$ alcohol benzoate were thoroughly admixed until the fumed silica was uniformly dispersed. The mixture then was transferred to a colloid mill and mixed for at least 2 minutes until homogeneous. The aluminum chlorohydrate and the hydrophobic starch derivative then were added to the mixture, and the resulting mixture was mixed until the aluminum chlorohydrate was completely dispersed. The suspending wax composition and the BENTONE GEL then were added to the mixture, and the resulting mixture was mixed until homogeneous. A premix of the dioctyl adipate and the fragrance then was added to the homogeneous mixture. The resulting mixture was returned to the colloid mill and mixed for at least 3 minutes. The composition then was mixed with a turbine propeller until the composition was uniform and homogeneous. The composition possessed physical properties suitable for use as a roll-on antiperspirant product. When topically-applied to the skin, the antiperspirant product was dry, as opposed to oily or sticky, and the antiperspirant product exhibited exceptional esthetic properties. However, because of the presence of an organoclay, i.e., the BENTONE GEL, this particular antiperspirant product demonstrated increased whitening and staining of the skin and clothes. The antiperspirant product showed negligible phase separation after a greater than one year aging period at 27° C.

EXAMPLE 8

| Ingredient | % (by weight) |
|---|---|
| Fumed silica[1] | 1.5 |
| Cyclomethicone[2] | 95.0 |
| Aluminum Zirconium Tetrachlorohydrex Glycinate[3] | 0.5 |
| Suspending Wax Composition[4] | 3.0 |

Procedure

The fumed silica was dispersed in the volatile liquid cyclomethicone, and the mixture was thoroughly blended until homogeneous. The aluminum chlorohydrate and the suspending wax composition then were added to the silica-silicone mixture, and the resulting mixture was charged through a colloid mill for at least two minutes until homogeneous. The resulting composition was a liquid having suitable physical properties, such as a 24 hour viscosity of about 3,200 cps and a seven day viscosity of about 3,400 cps, for use as a roll-on antiperspirant product. When topically-applied to the skin, the antiperspirant product was dry as opposed to oily or sticky; and the antiperspirant product exhibited excellent esthetic properties. The composition of Example 8 was a stable suspension demonstrating essentially no syneresis. Therefore, the composition of Example 8, including only 0.5% of the topically-active compound, demonstrates that it is the suspending agent, comprising the fumed silica and the suspending wax composition, that provides a stable dispersion as opposed to the topically-active compound. The composition of Example 8 can be compared to the compositions of Examples 1 through 7, each including 22% of the topically-active compound, to demonstrate that the suspending agent is the ingredient that provides a stable composition of the present invention.

EXAMPLE 9

| Ingredient | % (by weight) |
|---|---|
| Fumed silica[1] | 1.9 |
| Cyclomethicone[2] | 73.1 |
| Titanium Dioxide | 20.0 |
| Suspending Wax Composition[12] | 5.0 |

[12] The suspending wax contributes 1.5% castor wax, 1.65% dioctyl adipate and 1.85% cyclomethicone to the total weight of the composition.

Procedure

The fumed silica was dispersed in the volatile liquid cyclomethicone and the mixture was thoroughly blended until homogeneous. The suspending wax composition then was added to the silica-silicone mixture, and blended until homogeneous. The titanium dioxide was added, and the resulting mixture was charged through a colloid mill for at least two minutes until homogeneous. The resulting composition had an initial viscosity of about 85,000 cps, and therefore was suitable for use as a semisolid sunscreen product. When topically-applied to the skin, the sunscreen product was dry as opposed to oily or sticky; and the sunscreen product exhibited excellent esthetic qualities, with good spreading and coverage properties.

Alternate volatile silicones, and mixtures of volatile silicones, can be substituted for the particular volatile silicone carrier vehicle used in the preceding examples. Similarly, other finely-divided silica compounds, such as AEROSIL COLLOIDAL SILICA, available from Degussa Corp., Teterboro, NJ., can be substituted for the CAB-0-SIL brand of fumed silica.

To demonstrate the importance of including the suspending wax composition in a composition of the present invention as a preblend, as opposed to adding the ingredients of the suspending wax composition individually, the composition of Example 10 was prepared. The percentage of each individual ingredient included in the composition of Example 10 is identical to the percentage of each individual ingredient included in the composition of Example 1. However, in Example 10, the wax, the ester and the volatile carrier of the suspending wax composition were added to the topically-effective composition individually as opposed to a preblend prepared by the method described above.

EXAMPLE 10

| Ingredient | % (by weight) |
|---|---|
| Volatile Liquid Carrier[2] | 74.61 |
| Fumed Silica[1] | 1.50 |
| Castor Wax | 0.90 |
| Dioctyl Adipate | 0.99 |
| Aluminum Zirconium Tetrachlorohydrex Glycinate[3] | 22.00 |

Procedure

The first four ingredients were blended in the above-listed order of addition and under high shear. Then the antiperspirant compound was added to the homogeneous mixture under shear. It was found that the composition of Example 10 lacked the suspension properties and the esthetic properties demonstrated by the composition of Example 1, wherein the components of the suspending wax composition were preblended. In particular, it was observed that after the composition of Example 10 was topically applied, discrete, hard particles of castor wax were perceptible on the skin. In addition, syneresis was observed in the composition of Example 10 within a short time after preparation (i.e. within hours), and composition separate further over time.

The anhydrous, topically-effective compositions of the present invention, comprising a topically-active compound, like an antiperspirant compound; a suspending agent comprising finely-divided silica and a suspending wax composition; and a suitable volatile liquid carrier, exhibit unique and superior properties upon topical applications to skin or hair. The improved physical and sensory properties include ultra-dry characteristics, both as to feel and drying time; storage stability; elimination of the shaking requirement to redistribute the topically-active compound prior to use; substantially reduced whitening of the skin and clothing after topical application; and substantially reduced staining of clothing.

In addition, the new suspending agent of the present invention provides stable, anhydrous topically-effective compositions that effectively disperse and suspend insoluble, particulate ingredients and that resist phase separation over a greater than one year storage period. Surprisingly, the suspending agent includes less than 2% of a finely-divided silica and does not require an organoclay compound. Accordingly, the suspending agent improves the esthetics of the topically-effective composition.

It should be understood that the foregoing detailed description is given merely by way of illustration. Obviously, many modifications and variations of the invention as hereinbefore set forth can be made without departing from the spirit and scope thereof and therefore only such limitations should be imposed as are indicated by the appended claims.

What is claimed and desired to be secured by Letters Patent is:

1. An antiperspirant composition comprising:
   (a) about 0.01% to about 50% by weight of an antiperspirant compound;
   (b) from about 20% to about 98.89% by weight of a volatile liquid carrier selected from the group consisting of a cyclic volatile silicone having a viscosity of about 0.5 to about 10 centistokes, a linear volatile silicone having a viscosity of about 0.5 to about 10 centistokes, a volatile hydrocarbon including from about 10 to about 30 carbon atoms, and combinations thereof;
   (c) from about 0.1% to less than 2% by weight of a finely-divided silica; and
   (d) from about 1% to about 15% by weight of a suspending wax composition, wherein the suspending wax composition comprises from about 5% to about 50% by weight of a wax having a melting point of at least 150° F.; from about 0.1% to about 94.9% by weight of a volatile solvent selected from the group consisting of a volatile silicone, a volatile hydrocarbon and a combination thereof, wherein said volatile silicone has a viscosity of about 0.5 to about 10 centistokes and said volatile hydrocarbon includes from about 10 to about 30 carbon atoms; and from about 0.1% to about 94.4% by weight of an ester including at least 10 to about 32 carbon atoms, provided that the composition includes about 4.5% or less by weight of the wax.

2. The composition of claim 1 wherein the topically-active compound is an antiperspirant compound.

3. The composition of claim 2 wherein the antiperspirant compound is an astringent salt selected from the group consisting of an aluminum salt, a zirconium salt, a mixed aluminum zirconium salt, and mixtures thereof.

4. The composition of claim 3 wherein the antiperspirant compound is selected from the group consisting of aluminum zirconium tetrachlorohydrex glycinate, aluminum chlorohydrate, zirconium chlorohydrate, aluminum chlorohydrex, and mixtures thereof.

5. The composition of claim 1 wherein the volatile liquid carrier is present in the range from about 30% to about 75% by weight.

6. The composition of claim 1 wherein the cyclic volatile silicone has a viscosity at 25° C. in the range of from about 2 to about 6 centistokes and a boiling point at 25° C. and 760 mm in the range of from about 150° C. to about 250° C.

7. The composition of claim 7 wherein the cyclic volatile silicone is a cyclomethicone.

8. The composition of claim 8 wherein the cyclomethicone is selected from the group consisting of hexamethylcyclotrisiloxane, octamethylcyclotetrasiloxane, decamethylcyclopentasiloxane, dodecamethylcyclohexasiloxane, and mixtures thereof.

9. The composition of claim 1 wherein the linear volatile silicone has a viscosity at 25° C. in the range of from about 0.5 to about 5 centistokes and a boiling point at 2520 C. and 760 mm in the range of from about 100° C. to about 250° C.

10. The composition of claim 10 wherein the linear volatile silicone is selected from the group consisting of hexamethyldisiloxane, octamethyltrisiloxane, decamethyltetrasiloxane, dodecamethylpentasiloxane, and combinations thereof.

11. The composition of claim 1 wherein the volatile hydrocarbon includes from about 12 to about 24 carbon atoms and has a boiling point at 25° C. and 760 mm of from about 100° C. to about 300° C.

12. The composition of claim 12 wherein the volatile hydrocarbon has the structural formula:

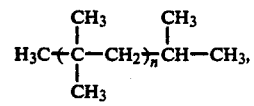

wherein n ranges from 2 to about 5, and mixtures.

13. The composition of claim 1 wherein the finely-divided silica is present in the range of from about 0.1% to about 1.5% by weight of the composition.

14. The composition of claim 1 wherein the finely-divided silica has an average particle size ranging from about 0.001 to about 0.05 microns.

15. The composition of claim 1 wherein the finely-divided silica is fumed silica.

16. The composition of claim 1 wherein the suspending wax composition is present in the range of from about 1.5% to about 10% by weight of the composition.

17. The composition of claim 1 wherein the ester of the suspending wax composition includes from about 12 to about 32 carbon atoms.

18. The composition of claim 1 wherein the ester of the suspending wax composition is selected from the group consisting of dioctyl adipate, neopentyl glycol dioctanoate, isodecyl neopentanoate, cetyl stearate, isocetyl stearate, a $C_{12}$–$C_{15}$ alcohol benzoate, and combinations thereof.

19. The composition of claim 1 wherein the ester of the suspending wax composition of dioctyl adipate.

20. The composition of claim 1 wherein the wax of the suspending wax composition is a synthetic wax, a natural wax or a combination thereof.

21. The composition of claim 1 wherein the wax of the suspending wax composition further comprises a wax having a melting point of less than 150° F.

22. The composition of claim 1 wherein the wax of the suspending wax composition is selected from the group consisting of castor wax, beeswax, carnauba wax, ozokerite wax, hydrogenated lanolin, cocoa butter, polyethylene, stearic acid, plamitic acid, microcrystalline wax, polyoxyethylene, bayberry wax, Japan wax, jojoba wax, mink wax, ouricury wax, rice bran wax, shellac wax, and combinations thereof.

23. The composition of claim 22 wherein the wax of the suspending wax composition is castor wax.

24. The composition of claim 1 wherein the volatile silicone of the suspending wax composition has a viscosity in the range of from about 0.5 to about 6 centistokes and a boiling point at 25° C. and atmospheric pressure of from about 100° C. to about 250° C.

25. The composition of claim 1 wherein the volatile hydrocarbon of the suspending wax composition includes from about 12 to about 24 carbon atoms and has a boiling point at 25° C. and 760 mm of from about 100° C. to about 300° C.

26. The composition of claim 1 wherein the volatile hydrocarbon of the suspending wax composition has the structural formula:

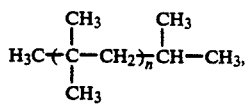

wherein n ranges from 2 to about 5, and mixtures.

27. The composition of claim 1 wherein the suspending wax composition comprises from about 25% to about 35% by weight castor wax; from about 30% to about 50% by weight of a volatile hydrocarbon having the structural formula:

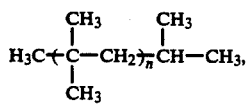

wherein n ranges from 2 to about 5; and from about 25% to about 50% by weight of dioctyl adipate.

28. The composition of claim 1 wherein the suspending wax composition comprises from about 25% to about 35% by weight castor wax; from about 30% to about 50% by weight of a cyclic volatile silicone, a linear volatile silicone or a combination thereof; and from about 25% to about 50% by weight dioctyl adipate.

29. The composition of claim 1 further comprising up to about 30% by weight of a suspending emollient.

30. The composition of claim 29 wherein the suspending emollient is selected from the group consisting of a nonvolatile silicone; an aromatic ester; an aliphatic ester; a high molecular weight polyol; an oil-soluble surfactant; and mixtures thereof.

31. The composition of claim 30 wherein the aromatic ester is a benzoate ester of an alcohol having from about 8 to about 30 carbon atoms.

32. The composition of claim 30 wherein the nonvolatile silicone is a dimethicone, a diphenylsiloxane fluid or a combination thereof.

33. The composition of claim 30 wherein the high molecular weight polyol is selected from the group consisting of polyoxyethylene (20) sorbitan monostearate polypropylene glycol and combinations thereof.

34. The composition of claim 30 wherein the oil-soluble surfactant is selected from the group consisting of decyl pyrrolidone, nonoxynol-2, and combinations thereof.

35. The composition of claim 30 wherein the aliphatic ester includes at least 10 to about 32 carbon atoms.

36. The composition of claim 1 further comprising from about 0.1% to about 10% by weight of a quaternized three-layer clay exfoliated with a polar solvent.

37. The composition of claim 36 wherein the quaternized three-layer clay is a quaternized montmorillonite clay exfoliated with propylene carbonate.

38. The composition of claim 1 further comprising an optional ingredient selected from the group consisting of from 0% to about 2% by weight of a drying agent; from 0% to about 10% by weight of an emollient; from 0% to about 5% by weight of a fragrance; and combinations thereof.

39. The composition of claim 38 wherein the drying agent is aluminum starch octenylsuccinate.

40. The composition of claim 39 wherein the emollient is selected from the group consisting of a fatty ether, a fatty alcohol, a mineral oil, a polyether siloxane copolymer, and combinations thereof.

41. The composition of claim 1 further comprising up to about 2% water.

42. An antiperspirant composition for application to the skin comprising:
(a) from about 0.01% to about 50% by weight of an antiperspirant compound;
(b) from about 20% to about 99.83% by weight of a volatile liquid carrier selected from the group consisting of a cyclic volatile silicone having a viscosity of about 0.5 to about 10 centistokes, a volatile hydrocarbon including from about 10 to about 30 carbon atoms and combinations thereof;
(c) from about 0.1% to less than 2% by weight of a finely-divided silica; and
(d) from about 0.05% to about 4.5% by weight of a wax having a melting point of at least 150° F.; and
(e) from about 0.01% to about 13.5% by weight of an ester including at least 10 to about 32 carbon atoms.

43. The composition of claim 42 wherein the finely-divided silica is present in the range of from about 0.1% to about 1.5% by weight of the composition.

44. The composition of claim 42 wherein the wax is a synthetic wax, a natural wax or a combination thereof.

45. The composition of claim 42 wherein the ester includes from about 12 to about 32 carbon atoms.

46. The composition of claim 42 further comprising from 0% to about 30% by weight of a suspending emollient selected from the group consisting of a nonvolatile silicone; an aromatic ester; an aliphatic ester; a high molecular weight polyol; an oil-soluble surfactant; and mixtures thereof.

* * * * *

UNITED STATES PATENT AND TRADEMARK OFFICE
CERTIFICATE OF CORRECTION

PATENT NO. : 5,292,530

DATED : March 8, 1994

INVENTOR(S) : McCrea et al.

It is certified that error appears in the above-identified patent and that said Letters Patent is hereby corrected as shown below:

Col. 9, line 32, "Dictionary." should be --Dictionary,--.

Col. 10, line 34, "2 or 3," should be --2 and 3,--.

Col. 10, line 46, "reducing the" should be --reducing and--.

Col. 12, line 10, "a paste.like" should be --a paste-like--.

Col. 14, line 27, "noepentyl" should be --neopentyl--.

Col. 15, line 41, "suspending was" should be --suspending wax--.

Col. 17, line 51, "was dry to opposed" should be --was dry as opposed--.

Col. 23, line 34, "about 94.4%" should be --about 94.9%--.

Col. 23, line 44, "claim 3" should be --claim 2--.

Col. 23, line 57, "claim 7" should be --claim 6--.

Col. 23, line 59, "claim 8" should be --claim 7--.

Col. 23, line 67, "at 2520C." should be --at 25°C--.

Col. 24, line 1, "claim 10" should be --claim 9--.

Col. 24, line 10, "claim 12" should be --claim 11--.

Col. 25, line 48, "rate polypropylene" should be --rate, polypropylene--.

UNITED STATES PATENT AND TRADEMARK OFFICE
CERTIFICATE OF CORRECTION

PATENT NO. : 5,292,530
DATED : March 8, 1994
INVENTOR(S) : McCrea, et al

It is certified that error appears in the above-indentified patent and that said Letters Patent is hereby corrected as shown below:

Col. 26, line 17, "claim 39" should be --claim 38--.

Signed and Sealed this

Eighteenth Day of October, 1994

Attest:

BRUCE LEHMAN

*Attesting Officer*         *Commissioner of Patents and Trademarks*